United States Patent [19]

Schönafinger et al.

[11] Patent Number: 5,006,540
[45] Date of Patent: Apr. 9, 1991

[54] SUBSTITUTED 3-AMINOSYDNONIMINES, PROCESSES FOR THEIR PREPARATION AND THEIR USE

[75] Inventors: Karl Schönafinger, Alzenau; Rudi Beyerle, Frankfurt; Melitta Just, Nidderau; Helmut Bohn, Schöneck; Jörg Ostrowski, Rodenbach, all of Fed. Rep. of Germany

[73] Assignee: Cassella Aktiengesellschaft, Frankfurt, Fed. Rep. of Germany

[21] Appl. No.: 422,502

[22] Filed: Oct. 17, 1989

[30] Foreign Application Priority Data

Nov. 3, 1988 [DE] Fed. Rep. of Germany ....... 3837327

[51] Int. Cl.$^5$ .................. C07D 271/04; A01K 31/41
[52] U.S. Cl. ...................................... 514/361; 548/125
[58] Field of Search ...................... 548/125; 514/361

[56] References Cited

U.S. PATENT DOCUMENTS 3,812,128  5/1974  Masuda ............................. 548/125

FOREIGN PATENT DOCUMENTS 706016  2/1970  Japan .................................. 548/125
1198283  7/1970  United Kingdom ............... 548/125

*Primary Examiner*—Robert Gerstl
*Attorney, Agent, or Firm*—Perman & Green

[57] ABSTRACT

Substituted 3-aminosydnonimines of the formula I

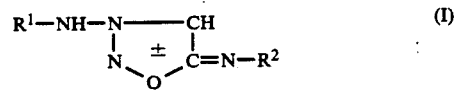

and their pharmacologically acceptable acid addition salts, wherein $R^1$ denotes, for example, alkyl having 1 to 8 C atoms, $R^2$ denotes hydrogen or the radical —$COR^3$ and $R^3$ denotes, for example, an aliphatic radical having 1 to 4 C atoms, are prepared, for example, by cyclization of a compound of the formula II

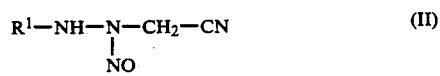

and if appropriate subsequent acylation and have useful pharmacological properties.

11 Claims, No Drawings

SUBSTITUTED 3-AMINOSYDNONIMINES, PROCESSES FOR THEIR PREPARATION AND THEIR USE

The invention relates to pharmacologically active substituted 3-aminosydnonimines of the general formula I

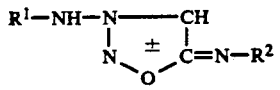

and their pharmacologically acceptable acid addition salts, wherein $R^1$ denotes alkyl having 1 to 8 C atoms, cycloalkyl having 5 to 8 C atoms, it also being possible for the alkyl or cycloalkyl radical to be substituted by —OR or —N($R^5$, $R^6$), or adamantyl, $R^2$ denotes hydrogen, —NO or the radical —$COR^3$, $R^3$ denotes an aliphatic radical having 1 to 6 C atoms, which can also be substituted by alkoxy having 1 to 6 C atoms or by an aliphatic thio radical having up to 4 C atoms; a cycloaliphatic radical having 5 to 7 C atoms; a bicycloaliphatic radical having 7 to 14 C atoms; a tricycloaliphatic radical having 7 to 16 C atoms; an alkoxy radical having 1 to 6 C atoms, which can also be substituted by alkoxy having 1 to 6 C atoms; an aryloxy radical having 6 to 10 C atoms; an alkoxycarbonyl radical having a total of 2 to 7 C atoms; an aryl radical having 6 to 10 C atoms; an aryl radical having 6 to 10 C atoms which is mono-, di- or trisubstituted by 1 to 3 halogen atoms and/or 1 to 3 alkyl radicals having 1 to 3 C atoms and/or 1 to 3 alkoxy radicals having 1 to 3 C atoms and/or 1 or 2 nitro groups and/or 1 or 2 hydroxyl groups and/or 1 or 2 alkylcarbonyloxy radicals having 1 to 4 atoms; or imidazolyl and $R^4$, $R^5$, $R^6$ denote hydrogen or alkyl having 1 to 6 C atoms.

The invention furthermore relates to a process for the preparation of the compounds according to the invention and their use.

Aliphatic radicals, alkyl radicals, alkoxy radicals, alkylamino radicals and dialkylamino radicals can be straight-chain or branched. This also applies if they occur as substituents of other radicals.

The alkyl radicals $R^5$ and $R^6$ can be identical or different.

Examples of $R^1$ are: methyl, ethyl, n-propyl, i-propyl, n-, i-, sec.- and tert.-butyl, n- and i-pentyl, n- and i-hexyl, n- and i-heptyl, n- and i-octyl, cyclopentyl, cyclohexyl, cycloheptyl, cyclooctyl, 2-hydroxyethyl, 2- or 3-hydroxypropyl, 2-, 3- or 4-hydroxybutyl, 3-, 4- or 5-hydroxy-2-methyl-pentyl, 2-methoxy-, -ethoxy-, -propoxy-ethyl, 3-methoxy-, -ethoxy-, -propoxy-propyl, 3-isopropoxy-propyl, 4-butoxy-butyl, 2-amino-, -dimethylamino-, -diethylamino-, -methylethyl-amino- or -methylpropylamino-ethyl, 4-dibutylamino-butyl, 2- or 3-hydroxycyclopentyl, 2- 3- or 4 hydroxycyclohexyl, 2-, 3- or 4-hydroxycycloheptyl, 2-, 3-, 4- or 5 hydroxycyclooctyl, 2-, 3- or 4-methoxy-, -ethoxy-, -propoxy-, -butoxycyclohexyl, 2-, 3- or 4-amino-, -dimethylamino-, -diethylamino-, or -methylethylamino-cyclohexyl, and 1-adamantyl.

Preferred radicals for $R^1$ are: alkyl having 1 to 6 C atoms, and furthermore hydroxyalkyl having 2 to 6 C atoms, cyclohexyl and hydroxycyclohexyl, in particular 2-hydroxycyclohexyl, and adamantyl.

Particularly preferred radicals for $R^1$ are: methyl, ethyl, i-propyl, neopentyl, cyclohexyl, 2-hydroxyethyl, adamantyl and 2-hydroxycyclohexyl, of which ethyl, i-propyl, cyclohexyl, 2-hydroxycyclohexyl and 1-adamantyl are especially preferred.

Preferred radicals for $R^2$ are: hydrogen, acetyl, propionyl, i-propylcarbonyl, tert.-butylcarbonyl, cyclohexylcarbonyl, benzoyl, 4-chlorobenzoyl, methoxycarbonyl, ethoxycarbonyl, i-propoxycarbonyl, butoxycarbonyl, allylthiomethylcarbonyl.

Possible aliphatic radicals $R^3$ are, in particular, alkyl radicals, preferably having 1 to 4 C atoms. The aliphatic radicals $R^3$, in particular the alkyl radicals, can also be substituted by alkoxy having 1 to 6 atoms, in particular 1 to 4 C atoms and preferably 1 to 3 C atoms. Examples of alkyl and alkoxyalkyl radicals which can be represented by $R^3$ are: methyl; ethyl; n-propyl; i-propyl; n-, i-, sec.- and tert.-butyl; n- and i-pentyl; n- and i-hexyl; methoxy-, ethoxy-, ni-propoxy-, i-propoxy-, n-butoxy-, i-butoxy-methyl; 2-methoxy-, 2-ethoxy-, 2-n-propoxy-, 2-i-propoxy-, 2-n-butoxy-ethyl; 2-methoxy-, 3-ethoxy-, 3-n-propoxy-, 3-i-propoxypropyl or -i-propyl. The aliphatic radicals $R^3$, in particular the alkyl radicals, can also be substituted by a thio radical having up to 4 C atoms and having aliphatic substituents. Such aliphatic thio radicals are, for example, alkylthio radicals having 1 to 4 C atoms, such as, for example, methyl-, ethyl-, n-propyl-, i-propyl-, n-butyl- and tert.-butyl-thio, but preferably allylthio ($CH_2$=CH—$CH_2$—S—). Possible cycloaliphatic radicals $R^3$ are, above all, cycloalkyl radicals having 5 to 7 C atoms, in particular cyclopentyl, and preferably cyclohexyl. A possible bicycloaliphatic radical $R^3$ is, in particular, 2,6,6-trimethylbicyclo(3.1.1.)heptan-3-yl (=pinan-3-yl). A possible tricycloaliphatic radical $R^3$ is, in particular, tricyclo $(3.3.1.1^{3.7})$decan-1-yl (=adamantyl).

The alkoxy radicals $R^3$ have, in particular, 1 to 4 C atoms, preferably 1 or 2 C atoms. The alkoxy substituents for the alkoxy radicals have, in particular, 1 to 4 C atoms. Examples of alkoxy radicals and alkoxyalkoxy radicals which can be represented by $R^3$ are: methoxy; ethoxy; n- and i-propoxy; n-, i-, sec.- and tert.-butoxy; n-pentoxy; i-hexoxy; methoxy-, ethoxy-, n-propoxy-, i-propoxy-, n-butoxy-methoxy; 2-methoxy-, 2-ethoxy-, 2-n-propoxy-, 2-i-propoxy-ethoxy; 3-methoxy-, 3-ethoxy-, 3-n-propoxy-, 3-i-propoxy-propoxy; 4-methoxy-, 4-ethoxy-, 4-n-propoxy-, 3-propoxy-, 4-n-butoxy-butoxy.

The alkoxycarbonyl radical $R^3$ preferably has 2 to 5 C atoms. Examples which may be mentioned here are: methoxy-, ethoxy-, n-propoxy-, i-propoxy-, n-butoxy-, and i-butoxy-carbonyl. A possible alkoxycarbonyl radical $R^3$ is, in particular, the ethoxycarbonyl radical.

Aryl radicals $R^3$ which may be mentioned are, for example α- or β-naphthyl radicals, but in particular the phenyl radical. Aryloxy radicals $R^3$ which may be mentioned are, for example, α- or β-naphthoxy radicals, but in particular the phenoxy radical. The aryl radicals $R^3$ can be mono-, di- or trisubstituted, but even in the case of trisubstitution, only at most 2 nitro groups may be present, such as, for example, 2-methyl-4,6-dinitrophenyl and 2-chloro-6-methyl-4-nitrophenyl. Possible halogen substituents for the aryl radicals are, for example, fluorine, chlorine and/or bromine atoms. Alkylcarbonyloxy substituents which may be mentioned for the aryl radicals, in particular for a phenyl radical, are, for example: acetoxy, n-propionyloxy, i-propionyloxy, n-butyryloxy and i-butyryloxy.

Examples of the optionally substituted aryl radicals $R^3$ are: phenyl, 2-, 3- or 4-methyl-, -ethyl-, -n-propyl- or -i-propylphenyl; 2-, 3- or 4-methoxy-, -ethoxy-, -n-propoxy- or -i-propoxyphenyl; 2-, 3- or 4-fluoro-, -chloro- or -bromo-phenyl; 2-, 3- or 4-nitrophenyl; 2-, 3- or 4-hydroxyphenyl; 2-, 3- or 4-acetoxy-, -n-propionyloxy- or -n-butyryloxy-phenyl; 2,3-, 2,4-, 2,5- or 2,6-dimethyl-, -diethyl-, or -dipropyl-phenyl; 2- or 3-methyl-4-chlorophenyl; and 2- or 3-ethyl-4-fluorophenyl; 2-chloro-4-ethylphenyl; 2-bromo-4-i-propylphenyl; 2,6-diethoxy-4-chlorophenyl; 2,3,4-, 3,4,5- or 2,3,5-trimethyl-, -triethyl-, -tripropyl-, -trimethoxy-, -triethoxy- or -tripropoxy-phenyl; 2-hydroxy-3-, -4- or -5-chlorophenyl; 2-methyl-3-, -4- or -5-acetoxy-phenyl.

Substituted aryl radicals $R^3$ which may be mentioned in particular are: methylphenyl (=tolyl), nitrophenyl and chlorophenyl. The imidazolyl radical $R^3$ is preferably a 1-imidazolyl radical.

Preferred radicals $R^3$ are: methyl, ethyl, cyclohexyl, phenyl, 4-chlorophenyl, 4-nitrophenyl, methoxy, ethoxy, n-propoxy, i-propoxy, 2-n-propoxy-ethoxy, 2-i-propoxy-ethoxy, n-butoxymethyl, 2-n-butoxy-ethoxy and allylthiomethyl.

$R^4$ preferably denotes hydrogen. The alkyl radicals $R^4$, $R^5$ and $R^6$ preferably have 1 to 4 C atoms.

A compound of the formula I can be prepared by a process in which (a) a compound of the general formula II

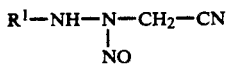   (II)

wherein $R^1$ has the meaning already given, is cyclized to give a compound of the general formula Ia

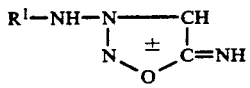   (Ia)

and in which this compound or an acid addition salt thereof, in the case where a compound of the formula I where $R^2$ = -$COR^3$ is to be prepared, is acylated with an acylating agent which introduces the radical -$COR^3$, or, in the case where a compound of the formula I where $R^2$ = -NO is to be prepared, is nitrosated, and if appropriate the compound thus obtained is converted into a pharmacologically acceptable acid addition salt, or in which (b) the tert.-butyl radical from a 3-aminosydnonimine of the formula III

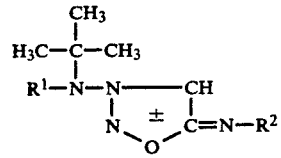   (III)

wherein $R^1$ and $R^2$ have the meanings already given, which can also be in the form of an acid addition salt, is split off and replaced by hydrogen, a compound of the formula Ia usually initially being formed, which—in the case where a compound of the formula I where $R^2$ = -$COR^3$ is to be prepared—as described above under (a), directly or in the form of an acid addition salt, is acylated with an acylating agent which introduces the radical -$COR^3$, or, in the case where a compound of the formula I where $R^2$ = -NO is to be prepared, is nitrosated, and if appropriate the compound thus obtained is converted into a pharmacologically acceptable acid addition salt.

The preparation of the compounds of the formula I according to the invention by process variant (b) is preferred.

The cyclization of the compound II to give the compound Ia is carried out in a suitable organic or inorganic solvent, dispersing agent or diluent with the addition of a cyclizing agent, usually at temperatures from −10° to 40° C., in particular 0° to 40° C. and preferably at 0° to 20° C.

Suitable cyclizing agents are those which establish a pH of 3 or less in aqueous solution, that is to say, for example, strong acids, such as mineral acids, such as sulphuric, nitric or phosphoric acid, but preferably hydrochloric acid, and also strong organic acids, such as trifluoroacetic acid. The cyclization is usually carried out while cooling with ice. 0.1 to 10 mol, preferably 1 to 5 mol, for example, of the cyclizing agent per mol of the compound of the formula II are used. The cyclizing agent is usually employed in excess. The use of hydrogen chloride as a cyclizing agent, which is usually passed into the reaction batch until this is saturated, is particularly convenient. The corresponding acid addition salt of the compound Ia is usually obtained during the cyclization.

Suitable solvents, dispersing agents or diluents are, for example: alcohols, for example those having 1 to 8 C atoms, in particular those having 1 to 6 C atoms, preferably those having 1 to 4 C atoms, such as, for example, methanol, ethanol, i- and n-propanol, i-, sec.- and tert.-butanol, n-, i-, sec.-, tert.pentanol, n-hexanol, 2-ethylbutanol, 2-ethylhexanol, isooctylalcohol, cyclopentanol, cyclohexanol, methylcyclohexanol (mixture) and benzylalcohol; ethers, in particular those having 2 to 8 C atoms in the molecule, such as, for example, diethylether, methyl ethyl ether, di-n-propyl ether, di-isopropyl ether, methyl n-butyl ether, methyl tert.-butyl ether, ethyl propyl ether, di-butyl ether, tetrahydrofuran, 1,4-dioxane, 1,2-dimethoxyethane and bis-β-methoxyethyl ether; oligoethylene glycol dimethyl ethers, such as, for example, tetraglyme or pentaglyme; carboxylic acid alkyl esters, in particular those having 2 to 10 C atoms in the molecule, such as, for example, methyl, ethyl, butyl or isobutyl formate, methyl, ethyl, propyl, isopropyl, butyl, isobutyl or sec.-butyl, amyl, isoamyl, hexyl, cyclohexyl or benzyl acetate and methyl, ethyl or butyl propionate; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone and acetophenone; aliphatic hydrocarbons, such as, for example, hexane, heptane, low- and high-boiling petroleum ethers, special benzines and white spirit; cycloaliphatic hydrocarbons, such as, for example, cyclopentane, cyclohexane, methylcyclohexane, tetralin and decalin; aromatic hydrocarbons, such as, for example, benzene, toluene, o-, m- and p-xylene and ethyl benzene; halogenated aliphatic or aromatic hydrocarbons, such as, for example, methylene chloride, chloroform, carbon tetrachloride, 1,2-dichloroethane, chlorobenzene and dichlorobenzene; hexamethylphosphoric acid triamide; sulfoxides, such as, for example, dimethyl-sulfoxide; tetramethylene sulfone; and water. Mixtures of various solvents or dispersing agents can also be used, for example water-methanol or, preferably, ethyl acetate-methanol.

The compounds of the formula Ia are compounds of the general formula I according to the invention in the case where $R^2$=hydrogen.

The acylation of the compound of the formula Ia, which can also be in the form of an acid addition salt, for introduction of the radical $R^2$=-$COR^3$ can be carried out in a manner which is known per se using a suitable acylating agent of the formula IV

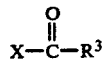
(IV)

wherein X represents a radical which can be split off nucleophilically.

In formula IV, X denotes, for example, in particular halogen, preferably -Cl or -Br; -OH; -O-alkyl, in particular having 1 to 5 C atoms; -O-aryl, the aryl radical being, in particular, a phenyl radical, which can also have one or more substituents from the group comprising alkyl, in particular methyl, and/or nitro, and is, for example, a tolyl, dinitrophenyl or nitrophenyl radical; —O—CO—$R^3$; —O—CO—O—alkyl, in particular having 1 to 5 C atoms in the alkyl radical, or the radical, bonded via an N atom of an azole or benzazole having at least 2 N atoms in the quasi-aromatic five-membered ring.

The acylation is advantageously carried out in the liquid phase in the presence of an inert solvent, dispersing agent or diluent or in an excess of the acylating agent, advantageously while stirring.

During the acylation, the molar ratio between the compound of the formula Ia and the acylating agent of the formula IV is theoretically 1:1. The acylating agent of the formula IV is advantageously employed in a slight molar excess. Excesses of up to 30 mol % are as a rule adequate, that is to say the molar ratio between the compound of the formula Ia and the acylating agent of the formula IV is usually 1 : (1 to 1.3), preferably 1 : (1 to 1.2). If an acid is split off during the acylation reaction, it is advantageous to add an acid-trapping agent, such as, for example, an alkali metal hydroxide, such as, for example, sodium hydroxide, potassium hydroxide or lithium hydroxide, a tertiary organic amine, such as, for example, pyridine or triethylamine, an alkali metal carbonate or alkali metal bicarbonate, such as, for example, sodium carbonate or sodium bicarbonate, or an alkali metal salt of a weak organic acid, such as, for example, sodium acetate. Suitable catalysts, such as, for example, 4-dimethylaminopyridine, can also be added during the acylation reaction.

The acylation can on principle be carried out at temperatures between $-10°$ C. and the boiling point of the solvent, dispersing agent or diluent used. In many cases, the reaction is carried out at 0° to 50° C., in particular at 0° to 30° C., and preferably at room temperature.

The compounds of the formula IV are acylating agents and are thus, for example: for X=halogen, acid halides or haloformic acid esters, of which acid chlorides and chloroformic acid esters are preferred; for —OH, carboxylic acids; for —O—alkyl and —O—aryl, esters, of which the tolyl or 2,4-dinitro- or 4-nitrophenyl esters are preferred; for —O—CO—$R^3$, anhydrides; for —O—CO—O—alkyl, mixed carboxylic acid/carbonic acid anhydrides; or heterocyclic amides or azolides, in particular of N,N'-carbonyldiazoles, such as, for example, N,N'-carbonyldiimidazole,2,2'-carbonyl-di-1,2,3-triazole, 1,1'-carbonyl-di-1,2,4-triazole, N,N'-carbonyl-dipyrazole or 2,2'-carbonyl-ditriazole (compare, for example, H. A. Staab, M. Lucking and F. H. Dürr, Chem. Ber. 95, (1962), 1275 pp; H. A. Staab and A. Mannschreck, Chem. Ber. 95, (1962), 1284 pp; and H. A. Staab and W. Rohr, "Synthesen mit heterocyclischen Amiden (Azoliden) (Syntheses with heterocyclic amides (azolides)" in "Neuere Methoden der Präparativen Organischen Chemie (Recent methods of preparative organic chemistry)", Volume 5, Verlag Chemie, 1967, page 53 et. seq., in particular pages 65 to 69). The acylating agents of the formula IV can be prepared by processes which are known per se.

If a carboxylic acid is used as the acylating agent, it is advantageous to add an activating agent, which has the task of increasing or activating the acylating potential of the carboxylic acid or of converting the carboxylic acid into a reactive carboxylic acid derivative of the formula IV in situ or, preferably, shortly before the reaction with the compound of the formula Ia. Suitable activating agents of this type are, for example: N,N'-disubstituted carbodiimides, especially if they contain at least one secondary or tertiary alkyl radical, such as, for example, diisopropyl-, dicyclohexyl- or N-methyl-N'-tert.butylcarbodiimide (compare Methodicum Chimicum, Verlag G. Thieme, Stuttgart, Volume 6, (1974), page 682/683 and Houben-Weyl, Methoden der Org. Chemie, (Methods of Organic Chemistry), Volume 8, (1952), pages 521/522); carbonic acid derivatives, such as, for example, phosgene or chloroformic acid esters, in particular having 1 to 5 C atoms in the alkyl radical (compare, for example, Tetrahedron Letters 24 (1983), 3365 to 3368); and carbonic acid esters, such as, for example, N,N'-disuccinimido-carbonate, diphthalimido-carbonate, 1,1'-(carbonyldioxy)-dibenzo-triazole or di-2-pyridyl carbonate (compare, for example, Tetrahedron Letters, Volume 25, No. 43, 4943-4946), if appropriate in the presence of suitable catalysts, such as, for example, 4-dimethylaminopyridine. Activating agents which are furthermore suitable are N,N'-carbonyldiazoles, such as, for example, N,N'-carbonyldiimidazole, 2,2'-carbonyl-di-1,2,3-triazole, 1,1'-carbonyl-di-1,2,4-triazole, N,N'-carbonyl-dipyrazole, 2,2'-carbonyl-ditetrazole, N,N'-carbonyl benzimidazole or N,N'-carbonylbenztriazole (compare, for example, H. A. Staab, M. Lücking and F. H. Dürr, loc. cit; H. A. Staab and A. Mannschreck loc. cit.; and H. A. Staab and W. Rohr loc. cit.). The commercially available N,N'-carbonyl-diimidazole is often used as the N,N'-carbonyl-diazole. However, the other N,N'-carbonylazoles are also readily accessible from the particular azole and phosgene.

Activating agents which are furthermore suitable for carboxylic acids are: derivatives of oxalic acid, such as, for example, oxalyl chloride (compare, for example British Patent Specification 2,139,225) or N,N'-oxalyldiazoles, such as, for example, 1,1'-oxalyldi-imidazole, 1,1'-oxalyldi-1,2,4-triazole and 1,1'-oxalyldi-1,2,3,4-tetrazole (compare, for example, Shizuaka Murata, Bull. Chem. Soc. Jap. 57. 3597-3598 (1984)); methylethylphosphinic anhydride (compare, for example, German Offenlegungsschrift 3,101,427); diphosphorus tetraiodide (Chem. Lett. 1983, 449); dialkyl disulfite (Indian J. Chem. 21, 259 (1982)); or other reactive agents.

Suitable solvents, dispersing agents or diluents for the acylation are, for example, those which have been mentioned for carrying out the cyclization, and moreover also, for example, pyridine and amides, such as, for example, dimethylformamide. In addition to water, polar organic solvents, such as dimethylformamide, dimethylsulfoxide or pyridine, are preferred for the acylation. Solvent mixtures, such as, for example, a mixture of water and methylene chloride, are also suitable.

If a compound of the formula I where $R^2=-NO$ is to be prepared, a compound of the formula Ia, which can also be in the form of an acid addition salt, is nitrosated in a manner which is known per se, advantageously in a suitable inert solvent or solvent mixture, preferably in water, usually at temperatures of 0° to 40° C. and preferably at temperatures of 0° to 10° C. The nitrosation is carried out with nitrous acid, NO, NOCl or NO-containing gas mixtures. The nitrosation is advantageously carried out with nitrous acid, which is advantageously produced from an alkali metal nitrite, for example sodium nitrite, and an acid, in particular hydrochloric acid. It is advantageous to adjust the aqueous solution of the compound Ia to a pH of 1 to 3 with an acid, in particular hydrochloric acid, and to add the alkali metal nitrite dropwise, in the form of an aqueous solution, to the stirred and cooled solution of the compound.

To prepare a compound according to the invention by process variant (b), a 3-aminosydnonimine of the formula III, which can also be in the form of an acid addition salt, is treated with an acid. Catalytic amounts of acid are already sufficient for the treatment. However, it is also possible to employ a larger molar excess of acid. The 3-aminosydnonimine of the formula III or an acid addition salt thereof is usually brought into contact with an acid in a molar ratio of 1 : (0.1 to 5), preferably 1 : (0.1 to 0.5). This treatment is advantageously likewise carried out in a suitable organic or inorganic solvent, dispersing agent or diluent. The reaction temperature is usually 0° C. up to the boiling point of the reaction mixture, in particular 0° to 40° C. and preferably 0° to 20° C. For splitting off the tert.-butyl group, a compound of the formla III can be left to stand with an acid in a suitable solvent at room temperature for a prolonged period of time.

Possible solvents, dispersing agents or diluents for process variant (b) are, for example, those which have been mentioned for the cyclization by process variant (a).

Acids which can be used for splitting off the tert.-butyl group are, for example, the acids mentioned as cyclizing agents in the case of process variant (a).

In process variant (b), acid addition salts of the compounds of the formula Ia are obtained. The compounds of the formula Ia can be converted into other compounds of the formula I by the acylation or nitrosation already mentioned.

The substituted 3-amino-sydnonimines of the general formula I form acid addition salts with inorganic or organic acids. Inorganic or organic acids are suitable for the formation of such acid addition salts. Examples of suitable acids are hydrogen chloride, hydrogen bromide and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulfonic, citric or adipic acid, and naphthalene disulphonic acids, in particular naphthalene-1,5-disulphonic acid. Pharmacologically acceptable acid addition salts are preferred. The acid addition salts can be prepared in the customary manner by combining the components, advantageously in a suitable solvent or diluent.

In the synthesis of the compounds of the formula I the acid addition salts are usually obtained.

If $R^1$ denotes a bulky radical, such as, for example, a secondary or tertiary alkyl group or cycloalkyl, the starting compounds of the general formula II required for synthesis route (a) can be prepared in a manner which is known per se by Strecker's aminonitrile synthesis from hydrazines of the general formula V

$$R^1-NH-NH_2 \qquad (V)$$

wherein $R^1$ has the meaning already given, by reaction with formaldehyde and hydrocyanic acid or sodium cyanide in a suitable solvent, for example water, a compound of the general formula VI

$$R^1-NH-NH-CH_2-CN \qquad (VI)$$

initially being formed and being converted into the compound II by nitrosation. The nitrosation is carried out in a known manner in a suitable inert solvent or solvent mixture, preferably in water, usually at temperatures of 0° to 40° C., preferably at temperatures of 0° to 10° C. The nitrous acid here is usually produced from an alkali metal nitrite, for example sodium nitrite, and an acid, in particular hydrochloric acid. It is advantageous to bring the aqueous solution of the compound VI to a pH of 1 to 3 with an acid, in particular hydrochloric acid, and to add the alkali metal nitrite dropwise, in the form of an aqueous solution, to the stirred and cooled solution of the compound.

The solution of the compound II obtained by this procedure can be subjected directly to the cyclization reaction. Usually, however, it is appropriate first to take up the nitroso compound II in a suitable organic solvent and to carry out the cyclization to give the compound of the formula Ia in this solvent, if appropriate after addition of another solvent.

The preparation of the starting compounds of the formula V is known or can be carried out by processes which are known per se.

The starting compounds of the formula III required for process variant (b) can be prepared from compounds of the formula VII

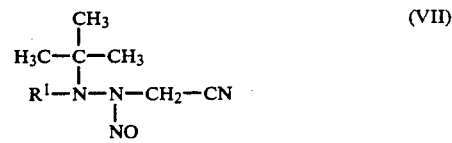

by cyclization, as has been described in the case of process variant (a). Since the cyclization is carried out by the action of acid, in the event of prolonged action of acid the splitting off of the tert.-butyl group occurs after the cylization has taken place. This means that process variant (b) can also be carried out directly after the synthesis of the compound III without the compound III being isolated.

The starting compounds of the general formula VII required can be prepared in a manner which is known per se by Strecker's aminonitrile synthesis from compounds of the general formula VIII

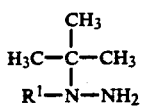

wherein $R^1$ has the meaning already given, by reaction with formaldehyde and hydrocyanic acid or sodium cyanide in a suitable solvent, for example water, a compound of the general formula IX

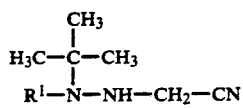

initially being formed and being converted into the compound VII by nitrosation and then cyclized, as has already been described in connection with the compounds of the formula VI in the case of process variant (a).

The compounds of the general formula VIII are known in some cases or can be prepared from compounds of the general formula X

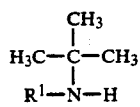

either by a process in which a compound of the formula X is nitrosated to give the N-nitroso compound XI, which is then reduced, advantageously with lithium aluminium hydride:

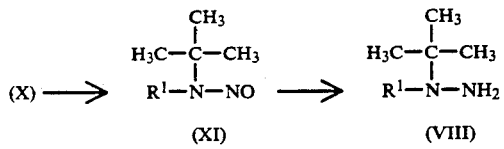

or by a process in which, in a manner which is known per se, a compound of the formula X is converted with potassium cyanate in an acid medium into the urea derivative XII, which is then converted into the compound XIII by oxidation with sodium hypochlorite by Hoffmann degradation.

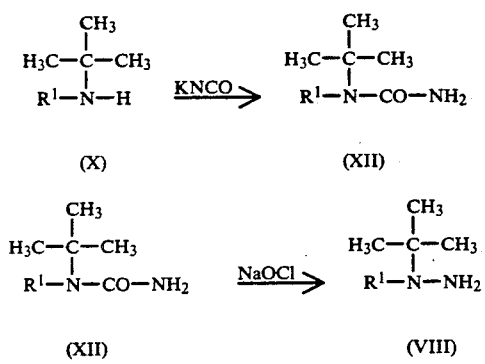

The preparation of the starting compounds of the formulae IV and X is known or can be carried out by processes which are known per se.

The compounds of the general formula I and III and their pharmacologically acceptable acid addition salts have useful pharmacological properties. Their action on the cardiovascular system is particularly pronounced. Compared with known sydnonimine compounds which are substituted in the 3-position, for example those of EP-B-59,356, and the commercially available structurally similar compound molsidomine, they surprisingly have a considerably more potent action and a longer duration of action. For example, they reduce blood pressure as well as the pulmonary arterial pressure and the left ventricular enddiastolic pressure, and thus contribute towards relieving cardiac activity in the sense of an antianginal action, without provoking reflectory tachycardia at the same time.

The compounds can also display antithrombotic effects by inhibition of platelet aggregation.

The compounds of the formula I and III and their pharmacologically acceptable acid addition salts can therefore be administered to humans as medicines by themselves, as mixtures with one another or in the form of pharmaceutical formulations which allow enteral or parenteral use and which contain, as the active constituent, an effective dose of at least one compound of the formula I or of an acid addition salt thereof, in addition to customary pharmaceutically acceptable excipients and additives.

The medicines can be administered orally, for example in the form of pills, tablets, lacquered tablets, coated tablets, hard and soft gelatin capsules, solutions, syrups, emulsions or suspensions or aerosol mixtures. However, they can also be administered rectally, for example in the form of suppositories, or parenterally, for example in the form of injection solutions, or percutaneously, for example in the form of ointments or tinctures.

Pharmaceutically inert inorganic or organic excipients can be used to prepare the pharmaceutical preparations. Lactose, maize starch or derivatives thereof, talc, stearic acid or salts thereof and the like, for example, can be used for the preparation of pills, tablets, coated tablets and hard gelatin capsules. Excipients for soft gelatin capsules and suppositories are, for example, fats, waxes, semi-solid and liquid polyols, naturally occurring or hardened oils and the like. Suitable excipients for the preparation of solutions and syrups are, for example, water, sucrose, invert sugar, glucose, polyols and the like. Suitable excipients for the preparation of injection solutions are, for example, water, alcohols, glycerol, polyols or vegetable oils.

In addition to the active compounds and excipients, the pharmaceutical preparations can also contain additives, such as, for example, fillers, extenders, disintegrating agents, binders, lubricants, wetting agents, stabilizers, emulsifiers, preservatives, sweeteners, colouring agents, flavouring agents or aromatizing agents, buffer substances and furthermore solvents or solubilizing agents or agents for achieving a depot effect, as well as salts for modifying the osmotic pressure, coating agents or antioxidants. They can also contain two or more compounds of the formula I or their pharmacologically acceptable acid addition salts, and in addition other therapeutically active substances.

Such other therapeutically active substances are, for example: β-receptor blockers, such as, for example, propranolol, pindolol and metoprolol; vasodilators, such as, for example, carbochromen; tranquillizers, such as, for example, barbituric acid derivatives, 1,4-benzodiazepines and meprobamate; diuretics, such as, for example, chlorothiazide; agents which tone the heart, such as, for example, digitalis preparations; hypotensive agents, such as, for example, hydralazine, dihydralazine, prazosine, clonidine and Rauwolfia alkaloids; agents which reduce the level of fatty acids in the blood, such as, for example, benzafibrate and fenofibrate; and agents for prophylaxis of thromboses, such as, for example, phenprocoumon.

The compounds of the formula I, their pharmacologically acceptable acid addition salts and pharmaceutical preparations which contain the compounds of the formula I or their pharmacologically acceptable acid addition salts as active compounds can be used on humans in combating or preventing diseases of the cardiovascular system, for example as antihypertensive medicines for the various forms of high blood pressure, in combating or preventing angina pectoris and the like. The dosage can be varied within wide limits and is to be adapted to the individual circumstances in each individual case. In general, a daily dose of about 0.5 to 100 mg, preferably 1 to 20 mg, per human individual is appropriate for oral administration. Because of the good absorption of the active compounds, the daily dose is also within similar amount ranges for other administration forms, that is to say in general likewise 0.5 to 100 mg/person. The daily dose is usually divided into several, for example 2 to 4, part administrations.

In the following examples, unless indicated otherwise, percentages are stated in percentages by weight. The ratios stated between components of solvents or mobile phases are volume ratios. The comment "decomp." denotes "decomposition".

EXAMPLE 1:

(a) 3-(2-Hydroxyethylamino)-sydnonimine hydrochloride 10 g of 3-(tert.-butyl-(2-hydroxyethyl)-amino)-sydnonimine hydrochloride are kept in 100 ml of 10% strength ethanolic hydrochloric acid at room temperature (20° C.) for 14 days. The mixture is stirred in an ice bath for 3 hours and the precipitate is filtered off with suction and recrystallized from ethanol. Yield: 5.0 g melting point: 145° C. (decomp.)

The 3-(tert.-butyl-(2-hydroxyethyl)-amino)-sydnonimine hydrochloride required as the starting substance is prepared as follows:

(b) N-Nitroso-tert.-butyl-(2-hydroxyethyl1-amine 23.4 g of 2-tert.-butylamino-ethanol are dissolved in 60 ml of water and 19.7 g of concentrated hydrochloric acid are added. A solution of 20.7 g of sodium nitrite in 30 ml of water is added dropwise at 30°–40° C. When the addition has ended, the mixture is heated at 70° C. for 1 hour and then stirred in an ice bath. The product is filtered off with suction or, in the case of the oily derivatives of the following examples, extracted by shaking with diethyl ether and the ether phase is dried and concentrated. Yield: 23.9 g melting point 65°–68° C.

(c) N-tert.-Butyl-N-(2-hydroxyethyl)-hydrazine

A total of 12.2 g of lithium alanate are added in portions to a mixture of 23 g of N-nitroso-tert.-butyl-(2-hydroxy-ethyl)amine and 200 ml of anhydrous tetrahydrofuran at 60° C. When the addition has ended, the mixture is heated at 60° C. for a further hour and cooled in an ice bath and the excess lithium alanate is hydrolysed by careful dropwise addition of methanol and then water. The solids are removed by filtration with suction and the filtrate is concentrated. A colourless oil (14 g) remains and is subsequently used without further purification.

(d) 3-(tert.-Butyl-(2-hydroxyethyl)-amino)-sydnonimine hydrochloride

The oil obtained in stage c (14 g) is dissolved in 50 ml of water and 8.1 g of concentrated hydrochloric acid and the solution is cooled to −5° C. A solution of 6.6 g of potassium cyanide in 20 ml of water is then added dropwise. After addition of 15 ml of ethanol, a 39% strength formalin solution (8.2 g) is added dropwise and the pH of the mixture is brought to 7. The mixture is stirred at room temperature for 2 hours and brought to pH 1.5 with concentrated hydrochloric acid, and a solution of 5.6 g of sodium nitrite in 25 ml of water is added dropwise, while cooling with ice. The mixture is subsequently stirred at room temperature overnight and then extracted with diethyl ether, and the extract is dried and concentrated. The oil which remains is dissolved in 50 ml of concentrated methanolic hydrochloric acid and the solution is diluted with 50 ml of ethyl acetate. The precipitate which has separated out is filtered off with suction and discarded. After 2 hours, the filtrate is concentrated, the residue is stirred with ethyl acetate and the solid is filtered off with suction and recrystallized from ethanol/diethyl ether (1:2). Yield: 5.9 g melting point=161°–163° C. (decomp.)

EXAMPLE 2:

3-Ethylamino-sydnonimine hydrochloride 14.5 g of 39% strength formalin are added to a solution of 26.55 g of N-tert.-butyl-N-ethyl-hydrazine hydrochloride and 9.38 g of sodium cyanide in 100 ml of water at 0° to 5° C. This mixture is stirred at room temperature for 16 hours, the pH being brought to 7 to 7.5. The pH is then brought to 1.0 by addition of concentrated hydrochloric acid, the mixture is cooled in an ice bath and a solution of 9.5 g of sodium nitrite in 20 ml of water is added dropwise. The nitroso compound formed is extracted with ether and the extract is dried and concentrated. The oil which remains is mixed with 10 ml of isopropanol, hydrogen chloride dissolved in ethyl acetate is added and the mixture is kept at room temperature for one day. The formation of the precipitate is intensified by cooling to 0° C. and the precipitate is filtered off with suction and recrystallized from isopropanol. Yield: 4.4 g melting point: 177° C. (decomp.)

EXAMPLE 3:

N-Ethoxycarbonyl-3-ethylamino-sydnonimine 7.5 g of sodium bicarbonate and then a solution of 5.8 g of ethyl chloroformate in 30 ml of methylene chloride are added to a solution, cooled to 0° C., of 7.9 g of 3-ethylamino-sydnonimine hydrochloride in 30 ml of water and the mixture is stirred at room temperature for 15 hours. The methylene chloride phase is separated off, dried and concentrated. The oil which remains is purified by column chromatography (silica gel; $CH_2Cl_2$:MeOH=98:2) and made to crystallize by stirring with diisopropyl ether. Yield: 4.6 g melting point: 131° C. (decomp.)

EXAMPLE 4:

3-Cyclohexylamino-sydnonimine hydrochloride

(a) N-Nitroso-tert.-butyl-cyclohexyl-amine

A mixture consisting of 13.2 ml of 10N hydrochloric acid, 50 ml of water, 18.8 g of tert.-butyl-cyclohexyl-amine and 17.9 g of sodium nitrite is heated at 90° C. for 3 hours. On cooling, a solid precipitates and is filtered off with suction. Yield: 16.3 g melting point: 87° C.

(b) N-tert.-Butyl-N-cyclohexyl-hydrazine hydrochloride

A mixture of 50 ml of tetrahydrofuran, 100 ml of dibutyl ether, 0.38 g of lithium alanate and 1.8 g of nitroso-tert.-butylcyclohexyl-amine is heated at the boiling point under nitrogen for 2 hours. 14.5 g of the nitroso compound, in one portion, and a total of 3.8 g of lithium alanate, in 3 portions, are then added in the course of 5 hours, during which the mixture is heated at 90° C. When the reaction has ended, the remaining lithium alanate is destroyed by careful dropwise addition of water, while cooling, the solid which forms is filtered off with suction and the filtrate is extracted by shaking with 2 portions of 1N hydrochloric acid (each 100 ml). The aqueous phase, which contains the hydrazine hydrochloride, is extracted by shaking with ether and the extract is employed for the next stage without further purification.

(c) N-tert.-Butyl-N-cyclohexyl-N'-cyanomethyl hydrazine

The solution, obtained under b, of the hydrazine hydrochloride is stirred in an ice bath and 4 g of sodium cyanide are added. The mixture is rendered neutral and 7.7 g of a 39% strength formalin solution are added dropwise The pH is brought to a value of 7 by addition of sodium carbonate solution, the mixture is stirred at room temperature for 2 hours and the product is extracted with diethyl ether. After drying and concentrating, a yellow oil remains and is employed for the next stage without further purification. Yield: 12.2 g

(d) 3-(tert.-Butyl-cyclohexyl-amino)-sydnonimine hydrochloride

The oil obtained under c is dissolved in 100 ml of water and 6 ml of 10N HCl are added. A solution of 6.9 g of sodium nitrite in 20 ml of water is then added dropwise and the mixture is subsequently stirred at room temperature for one hour. The nitroso intermediate stage is extracted by shaking with ethyl acetate (50 ml) and the ethyl acetate phase is dried and treated with excess ethereal hydrochloric acid at 0°-5° C. The oil which separates out is purified by column chromatography (silica gel, MeOH:CH$_2$Cl$_2$=1:9). After the corresponding fractions have been concentrated in a rotary evaporator, the residue is stirred with diethyl ether and the solid is filtered off with suction. Yield: 6.7 g melting point: 158° C. (decomp.)

(e) 3-Cyclohexylamino-sydnonimine hydrochloride

A solution of 4 g of 3-(tert.-butyl-N-cyclohexyl-amino)sydnonimine hydrochloride in 30 ml of concentrated ethanolic hydrochloric acid is left to stand at room temperature for one day and then concentrated in a rotary evaporator. The residue is purified by column chromatography (silica gel, CH$_2$Cl$_2$:MeOH=9:1) and the residue obtained after concentration of the corresponding fractions is stirred with isopropyl acetate and filtered off with suction. Yield: 2.5 g melting point: 90° C. (decomp.)

EXAMPLE 5

3-(2-Hydroxycyclohexyl-amino)-sydnonimine hydrochloride

(a) N-tert.-Butyl-N-(2-hydroxycyclohexyl)-hydrazine hydrochloride 10 g of lithium alanate are added in portions of 1 g to a solution of 38.8 g of N-nitroso-tert.-butyl-(2-hydroxycyclohexyl)amine (obtained by heating 1,2-epoxy-cyclohexane with tert.butylamine at 150° C. in an autoclave and then nitrosating the mixture with sodium nitrite/HCl) under a nitrogen atmosphere in the course of 2 days, the mixture being heated at 50° C. The residual lithium alanate is destroyed by cooling the mixture and careful dropwise addition of 50 ml of methanol and then 75 ml of water. The mixture is then filtered and the filtrate is concentrated. The residue is taken up in 100 ml of methylene chloride, the water which separates out is separated off and the organic phase is dried and concentrated again. The oil thus obtainable is dissolved in 20 ml of ethanol and 150 ml of tert.-butyl methyl ether, and the hydrazine hydrochloride is precipitated by addition of ethereal HCl. Yield: 28.5 g melting point: 145° C. (decomp.)

(b) 3-(2-Hydroxycyclohexyl-amino)-sydnonimine hydrochloride

A mixture of 13.35 g of N-tert.-butyl-N-(2-hydroxycyclohexyl)-hydrazine hydrochloride, 3.1 g of sodium cyanide and 50 ml of water is stirred in an ice bath and a 39% strength formalin solution (5.7 g) is added dropwise. The pH of the mixture is brought to 7 to 7.5 and the mixture is stirred at room temperature for 3 hours. The pH is then brought to 1 with concentrated hydrochloric acid and a solution of 6 g of sodium nitrite in 25 ml of water is added dropwise. After one hour, the nitroso compound is extracted with diethyl ether, the ethereal phase is dried and ethereal HCl is added. After 2 days, the precipitate is filtered off with suction and recrystallized from isopropanol/ethyl acetate. Yield: 4.5 g melting point: 174°-5° C. (decomp.)

EXAMPLE 6

N-Benzoyl-3-(2-hydroxycyclohexyl-amino)-sydnonimine

A solution of 1.45 g of benzoyl chloride in 20 ml of methylene chloride is added to a solution, cooled to 5° C., of 1.9 g of 3-(2-hydroxycyclohexyl-amino)-sydnonimine hydrochloride and 1.7 g of sodium bicarbonate in 20 ml of water, and the mixture is stirred in an ice bath for 4 hours. The precipitate is filtered off with suction and recrystallized from isopropanol. Yield: 1.6 g melting point: 174° C. (decomp.)

EXAMPLE 7

N-Cyclohexylcarbonyl-3-(2-hydroxycyclohexyl-amino)-sydnonimine

A solution of 3.3 g of cyclohexanecarbonyl chloride in 30 ml of methylene chloride is added to a solution, cooled to 5° C., of 3.5 g of 3-(2-hydroxy-cyclohexyl-amino)-sydnonimine hydrochloride and 2.6 g of sodium bicarbonate in 30 ml of water and the mixture is stirred at room temperature for 20 hours. The methylene chloride phase is separated off, dried and concentrated. The residue is recrystallized from isopropyl acetate. Yield: 2.6 g melting point: 155° C. (decomp.)

EXAMPLE 8

N-(4-Chlorobenzoyl)-3-(2-hydroxycyclohexyl-amino)-sydnonime

A solution of 3.5 g of 3-(2-hydroxycyclohexyl-amino)sydnonimine hydrochloride in 30 ml of water is cooled to 5° C., 2.6 g of sodium carbonate and a solution of 3.9 g of 4-chlorobenzoyl chloride in 30 ml of methylene chloride are added in succession and the mixture is stirred at room temperature for 20 hours. The organic phase is separated off, dried and concentrated. The oily residue is crystallized from di-n-propyl ether. Yield: 3.3 g melting point: 169° C. (decomp.)

EXAMPLE 9

N-Ethoxycarbonyl-3-(2-hydroxycyclohexyl-amino)-sydnonimine

This compound is prepared analogously to Example 8 from 7.6 g of 3-(2-hydroxycyclohexyl-amino)-sydnonimine hydrochloride, 3.4 g of ethyl chloroformate and 5.5 g of sodium bicarbonate and recrystallized from isopropyl acetate. Yield: 5.8 g melting point: 147° C.

The following examples A to F relate to pharmaceutical preparations.

EXAMPLE A

Soft gelatin capsules containing 5 mg of active compound per capsule:

|  | per capsule |
|---|---|
| Active compound | 5 mg |
| Triglyceride mixture fractionated from coconut fat | 150 mg |
| Capsule contents | 155 mg |

EXAMPLE B

Injection solution containing 1 mg of active compound per ml:

|  |  | per ml |
|---|---|---|
| Active compound |  | 1.0 mg |
| Polyethylene glycol 400 |  | 0.3 ml |
| Sodium chloride |  | 2.7 mg |
| Water for injection purposes | ad | 1 ml |

EXAMPLE C

Emulsion containing 3 mg of active compound per 5 ml

|  |  | per 100 ml of emulsion |
|---|---|---|
| Active compound |  | 0.06 g |
| Neutral oil |  | q.s. |
| Sodium carboxymethyl cellulose |  | 0.6 g |
| Polyoxyethylene stearate |  | q.s. |
| Pure glycerol |  | 0.2 to 2.0 g |
| Flavouring agent |  | q.s. |
| Water (desalinated or distilled) | ad | 100 ml |

EXAMPLE D

Rectal medicament form containing 4 mg of active compound per suppository

|  |  | per suppository |
|---|---|---|
| Active compound |  | 4 mg |
| Suppository base | ad | 2 g |

EXAMPLE E

Tablets containing 2 mg of active compound per tablet

|  | per tablet |
|---|---|
| Active compound | 2 mg |
| Lactose | 60 mg |
| Maize starch | 30 mg |
| Soluble starch | 4 mg |
| Magnesium stearate | 4 mg |
|  | 100 mg |

EXAMPLE F

Coated tablets containing 1 mg of active compound per coated tablet

|  | per coated tablet |
|---|---|
| Active compound | 1 mg |
| Maize starch | 100 mg |
| Lactose | 60 mg |
| Secondary calcium phosphate | 30 mg |
| Soluble starch | 3 mg |
| Magnesium stearate | 2 mg |
| Colloidal silicic acid | 4 mg |
|  | 200 mg |

The pharmacological action of the compound of the formula I has been determined by a modified method of Godfraind and Kaba (Arch. Int. Pharmacodyn. Ther. 196, (Suppl) 35 to 49, 1972) and of Schümann et al. (Naunyn-Schmiedeberg's Arch. Pharmacol. 289, 409 to 418, 1975). In this method, spiral strips of the arteria pulmonalis of the guinea pig are depolarized with 40 mmol/l of potassium after equilibration in calcium-free Tyrode solution. Addition of 0.5 mmol/l of $CaCl_2$ then induces a contraction. The relaxing action of the test substance is determined by cumulative addition of concentrations graduated in ½ log 10. The concentration of test substance which inhibits the contraction by 50% ($=IC_{50}$, mol/l) is determined from the concentration/effect curve (abscissa: -log mol/l of test substance, ordinate: % inhibition of the maximum contraction, mean value of 4 to 6 strips of vessel). The $IC_{50}$ values thus obtained are stated in the following table. As the comparison with the $IC_{50}$ value: $>1\times10^{-4}$ for the known compound molsidomine (N-ethoxycarbonyl-3-morpholino-sydnonimine), compare DE-B-1,695,897, shows, the values of the compounds of the formula I are considerably more favourable.

TABLE

| Compound of the formula I according to example | $IC_{50}$ (mol/l) |
|---|---|
| 1a | $2 \times 10^{-6}$ |
| 2 | $2 \times 10^{-6}$ |
| 4e | $2 \times 10^{-6}$ |

TABLE-continued

| Compound of the formula I according to example | IC$_{50}$ (mol/l) |
| --- | --- |
| 5b | $1 \times 10^{-6}$ |
| Molsidomine (N-ethoxycarbonyl-3-morpholino-sydnonimine) (Comparison substance) | $>1 \times 10^{-4}$ |

We claim: It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

1. Pharmacologically active substituted 3-aminosydnonimines of the general formula $$R^1-NH-N\underset{N\diagdown_O\diagup}{\overset{\pm}{\rule{1cm}{0.4pt}}}\underset{}{\overset{CH}{\underset{C=N-H}{|}}}$$

and their pharmacologically acceptable acid addition salts, wherein R$^1$ denotes ethyl, hydroxyethyl, hydroxycyclohexyl or adamantyl.

2. 3-(Adamant-1-yl)-amino-sydnonimine and its pharmacologically acceptable acid addition salts.

3. 3-(Adamant-1-yl)-amino-sydnonimine hydrochloride according to claim 2.

4. 3-(2-Hydroxycyclohexyl)-amino-sydnonimine and its pharmacologically acceptable acid addition salts.

5. 3-(2-Hydroxycyclohexyl)-amino-sydnonimine hydrochloride according to claim 4.

6. 3-(2-Hydroxyethylamino)-sydnonimine and its pharmacologically acceptable acid addition salts.

7. 3-(2-Hydroxyethylamino)-sydnonimine hydrochloride according to claim 6.

8. 3-Ethylamino-sydnonimine and its pharmacologically acceptable acid addition salts.

9. 3-Ethylamino-sydnonimine hydrochloride according to claim 8.

10. Process for using substituted 3-aminosydnonimines of claim 1 or their pharmacologically acceptable acid addition salts as pharmacological active compounds for combating and preventing cardiovascular disease, which comprises administering an effective amount thereof to a host in need thereof.

11. Pharmaceutical composition characterized in that it contains a compound of claim 1 or an acid addition salt thereof as the active compound, for combating and preventing cardiovascular diseases, together with pharmaceutically acceptable excipients and additives and, optionally, one or more other pharmacological active compounds.

* * * * *